(12) United States Patent
Carrol

(10) Patent No.: US 6,756,064 B1
(45) Date of Patent: Jun. 29, 2004

(54) THERAPEUTIC COMPOSITION

(76) Inventor: John William Carrol, P.O. Box 795, Wyong, New South Wales (AU)

( * ) Notice: Subject to any disclaimer, the term of this patent is extended or adjusted under 35 U.S.C. 154(b) by 0 days.

(21) Appl. No.: 09/621,307

(22) Filed: Jul. 20, 2000

(51) Int. Cl.⁷ ............................................... A61K 35/78
(52) U.S. Cl. .................... 424/742; 420/195.1; 514/886; 514/887; 514/944
(58) Field of Search .............................. 424/195.1, 742; 514/886, 887, 944

(56) References Cited

U.S. PATENT DOCUMENTS 5,431,924 A * 7/1995 Ghosh et al. ................ 424/522
5,795,573 A * 8/1998 Paradise ...................... 424/737
6,444,238 B1 * 9/2002 Weise ......................... 424/736

OTHER PUBLICATIONS

Skin Care and Cosmetic Ingredient Dictionary, p. 40.1994.*

* cited by examiner

Primary Examiner—Jyothsna Venkat
(74) Attorney, Agent, or Firm—Mark R. Wisner

(57) ABSTRACT

A therapeutic composition comprising: arnica, rosemary oil and emu oil.

2 Claims, No Drawings

THERAPEUTIC COMPOSITION

FIELD OF THE INVENTION

The present invention relates to a therapeutic composition and method for manufacture of same.

BACKGROUND OF THE INVENTION

Physical activity such as strenuous exercise can subject the human body to intense strains which may cause pain to result in their muscles and/or joints. For example, when a person runs, after a certain distance they may feel a distinct pain in their leg such as in their shin. This shin pain often occurs in the same spot.

Exercise causes the muscles to use more oxygen. If the circulation to the legs is partially or totally blocked, activities such as walking or climbing stairs cause muscle fatigue, pain or aching. Recurring pain, colloquially known as "leg cramp", may be the result of the muscles in the persons legs not receiving enough oxygen and nutrients due to poor or inefficient circulation.

Furthermore, an injury to the human body may cause inflammation wherein swelling occurs in a localised area of the body or arthritic pain in the joint due to wearing. Again, it is thought that increased circulation of the blood around the joint may facilitate the restoration of damaged tissue.

The applicant does not concede that the prior art discussed in this specification forms part of the common general knowledge in the art at the priority date of this application.

SUMMARY OF THE INVENTION

It is an object of the invention to provide an improved new composition to treat injured and inflamed parts of the body, or at least an alternative therapeutic composition to that known in the art.

According to a first aspect of the present invention, there is provided a therapeutic composition comprising: arnica, rosemary oil and emu oil.

The composition may further comprise any one or more of the following: eucalyptus oil; an alcohol and camphor.

The arnica may be arnica montana and/or arnica chamissonis foliosa.

The arnica montana may be present in the composition in the range from about 3% to about 35% by weight and more preferably in the range from about 4% to about 10% by weight.

The rosemary oil may be present in the composition in the range from about 3% to about 35% by weight and more preferably to about 13% by weight.

The emu oil may be present in the composition in the range from about 0.5% to about 37% by weight and more preferably is present in the composition to about 1.2% by weight.

The eucalyptus oil may be present in the composition in the range from about 0.4% to about 35% by weight and more preferably about 0.7% by weight.

The camphor may be present in the composition in the range from about 2.6% to about 35% by weight and more preferably about 3.8% by weight.

The alcohol may be ethanol and may be present in the composition in the range from about 3% to about 85% by weight and more preferably in the range from about 65% to about 68% by weight.

The composition may further comprises a fragrance.

The composition is preferably applied by applying it to the skin and massaging it therein.

The formulation may be a cream, gel, ointment, milk, lotion or solution.

The formulation may be applied to the skin in a spray, tincture, or solution in an alcoholic solvent.

According to another aspect of the present invention, there is provided a method of preparing a therapeutic composition comprising the step of:

(a) mixing arnica, rosemary oil and emu oil.

Optionally, the arnica and rosemary oil are preferably first mixed together for a about 8 to 12 minutes, afterwhich, the emu oil is mixed with the mixed arnica and rosemary oil for about 16 to 24 minutes.

The method may further comprise the step of:

(b) mixing eucalyptus oil to said arnica, rosemary oil and emu oil mixture.

The method may further comprises the step of:

(c) mixing a fragrance to said mixture of step (b).

The method may further comprises the step of:

(d) mixing an alcohol to said mixture of step (b) and step (d) may be performed for about 40 minutes.

According to yet another aspect of the present invention, there is provided a therapeutic composition comprising:

arnica in the range of about 3% to about 8% by weight;

rosemary oil in the range of about 3% to about 13% by weight;

emu oil in the range of about 3% to about 5% by weight; and a carrier medium.

Another aspect of the present invention provides a therapeutic composition comprising:

arnica in the range of about 3% to about 8% by weight;

rosemary oil in the range of about 3% to about 15% by weight;

emu oil in the range of about 3% to about 8% by weight;

eucalyptus oil in the range of about 3% to about 8% by weight;

camphor in the range of about 2.6% to about 3.4% by weight; and ethanol in the range of about 72% to about 85.3% by weight.

In the description and claims of this specification the word "comprise" and variations of that word, such as "comprises" and "comprising" are not intended to exclude other features, additives, components, integers or steps but rather, unless otherwise stated explicitly, the scope of these words should be construed broadly such that they have an inclusive meaning rather than an exclusive one.

DETAILED DESCRIPTION OF THE EMBODIMENTS

Notwithstanding any other forms which may fall within the scope of the present invention, preferred forms of the invention will now be described, by way of example only.

A preferred embodiment provides a therapeutic composition comprising arnica montana, rosemary oil and emu oil.

A solution of arnica montana, rosemary oil and emu oil is combination which provides a therapeutic effect to a persons joints and muscles especially after that person has undergone strenuous activity. Furthermore, this composition may also assist in the relief of the effects of arthritic pain. The solution is applied liberally to the skin and it is thought that this results in pain relief by increasing blood circulation within the vicinity of the affected area Furthermore, other ingredients may be added to the composition to enhance the properties, as will be explained below.

Solution 1

A preferred composition involves first preparing an initial 400 liters of concentrate, comprises the steps of:

Step 1

Preparing an Arnica Montana tincture solution consisting of 17.7% (wt) Arnica Montana herbs in a solution consisting of 45% (wt) ethanol and 55% (wt) water.

Step 2

Mixing 185 kg of the Arnica Montana tincture solution with 88 kg of Rosemary Oil in a mixing vat for 10 minutes.

Step 3

Adding 4.8 kg of Eucalyptus Oil and 8 kg of Emu Oil to the mixing vat and mixing for a further 20 minutes.

Step 4

Adding 76.4 kg of ethanol to the mixing vat and then mixing for a further 15 minutes.

Step 5

Adding a fragrance (such as Herbfresh) to the mixing vat to thereby provide an enhanced fragrance to the end product.

From Steps 1 to 5, a concentrate solution is formed of the composition shown in Table 1:

TABLE 1

| Additive | Mass (kg) | % (wt) |
|---|---|---|
| Arnica Montana | 32.9 | 10 |
| Rosemary Oil | 88.0 | 22 |
| Eucalyptus Oil | 4.8 | 1.2 |
| Emu Oil | 8.0 | 2 |
| Herbfresh | 14.4 | 6 |
| Water | 83.8 | 23.1 |
| Ethanol | 130.6 | 36 |
| Total | 362.5 | 100 |

After the concentrate has been manufactured, the final product which is sent to customers is further diluted by the addition of a further 315 kg (approx. 400 liters) of ethanol to produce a final composition as shown in Table 2:

Composition 1

TABLE 2

| Additive | Mass (kg) | % (wt) |
|---|---|---|
| Arnica Montana | 32.9 | 4.9 |
| Rosemary Oil | 88.0 | 13 |
| Eucalyptus Oil | 4.8 | 0.7 |
| Emu Oil | 8.0 | 1.2 |
| Herbfresh | 14.4 | 2.1 |
| Water | 83.8 | 12.4 |
| Ethanol | 445.6 | 65.8 |
| Total | 677.5 | 100 |

The final product of Table 2 is then placed into a 150 ml pump action spray bottles.

Other final compositions of product are shown in following tables

Composition 2

TABLE 3

| Additive | Mass (kg) | % (wt) |
|---|---|---|
| Arnica Montana | 32.9 | 4.9 |
| Rosemary Oil | 88.0 | 13 |
| Eucalyptus Oil | 4.8 | 0.7 |
| Emu Oil | 8.0 | 1.2 |
| Water | 83.8 | 12.4 |
| Ethanol | 460 | 67.9 |
| Total | 677.5 | 100 |

The solution in Table 3 does not have any Herbfresh fragrance added to it.

Composition 3

TABLE 4

| Concentrate | Mass (kg) | % (wt) |
|---|---|---|
| Arnica Montana | 20 | 3 |
| Rosemary Oil | 60 | 8.9 |
| Eucalyptus Oil | 4.5 | 0.7 |
| Emu Oil | 13 | 1.9 |
| Water | 60 | 8.9 |
| Ethanol | 520 | 76.8 |
| Total | 677.5 | 100 |

Composition 4

TABLE 5

| Concentrate | Mass (kg) | % (wt) |
|---|---|---|
| Arnica Montana | 50 | 7.4 |
| Rosemary Oil | 82 | 12.1 |
| Eucalyptus Oil | 9.0 | 1.3 |
| Emu Oil | 38.0 | 5.6 |
| Water | 78 | 11.5 |
| Ethanol | 420.5 | 62.1 |
| Total | 677.5 | 100 |

Composition 5

TABLE 6

| Concentrate | Mass (kg) | % (wt) |
|---|---|---|
| Arnica Montana | 68 | 10 |
| Rosemary Oil | 98 | 14.5 |
| Eucalyptus Oil | 36 | 5.3 |
| Emu Oil | 38 | 5.6 |
| Water | 84 | 12.4 |
| Ethanol | 353.5 | 52.2 |
| Total | 677.5 | 100 |

Composition 6

TABLE 7

| Concentrate | Mass (kg) | % (wt) |
|---|---|---|
| Arnica Montana | 98 | 14.5 |
| Rosemary Oil | 62 | 9.2 |
| Eucalyptus Oil | 36 | 5.3 |
| Emu Oil | 41 | 6.1 |
| Water | 116 | 17.1 |
| Ethanol | 324.5 | 47.9 |
| Total | 677.5 | 100 |

Composition 7

TABLE 8

| Concentrate | Mass (kg) | % (wt) |
| --- | --- | --- |
| Arnica Chasissonis Foliosa | 80 | 11.8 |
| Rosemary Oil | 120 | 17.7 |
| Eucalyptus Oil | 36 | 5.3 |
| Emu Oil | 35 | 5.2 |
| Camphor | 26 | 3.8 |
| Water | 116 | 17.1 |
| Ethanol | 264.5 | 39 |
| Total | 677.5 | 100 |

Composition 8

TABLE 9

| Concentrate | Mass (kg) | % (wt) |
| --- | --- | --- |
| Arnica Montana | 65 | 9.6 |
| Rosemary Oil | 72 | 10.6 |
| Eucalyptus Oil | 8.9 | 1.3 |
| Emu Oil | 6.4 | 0.9 |
| Herbfresh | 12 | 1.8 |
| Camphor | 15 | 2.2 |
| Water | 83.8 | 12.4 |
| Ethanol | 414 | 61.2 |
| Total | 677.5 | 100 |

Composition 10

TABLE 11

| Concentrate | Mass (kg) | % (wt) |
| --- | --- | --- |
| Arnica Montana | 165 | 24.4 |
| Rosemary Oil | 140 | 20.7 |
| Eucalyptus Oil | 135 | 19.9 |
| Emu Oil | 237.5 | 35.1 |
| Total | 677.5 | 100 |

Composition 11

TABLE 12

| Concentrate | Mass (kg) | % (wt) |
| --- | --- | --- |
| Arnica Montana | 210 | 31 |
| Rosemary Oil | 225 | 33.2 |
| Eucalyptus Oil | 242.5 | 35.8 |
| Total | 677.5 | 100 |

The presence of the ethanol effects the rheological properties of the solution by reducing the overall viscosity of the solution and assisting the application of the solution from the pump action spray when it is applied to a person's skin. It is also thought that the ethanol may act as a nerve block in relieving pain.

The solution is liberally applied to the person's skin by the pump action spray around the region from where pain emanates and the solution can then be lightly rubbed into the skin. A second additional spray can be applied in another 30 seconds and the treatment continued three times daily. Application of the solution will depend upon the particular problem for which it is being applied. When the solution is applied to painful joints, pain relief usually ensues for acute pain within about 1 to 5 minutes. For arthritic pain, where the joints are badly swollen, the solution should be applied four times a day for seven to ten days.

It is thought that the solution facilitates an increase in blood circulation within the vicinity of its application. This increase in circulation facilitates the restoration of damaged muscle tissue, relaxes muscles and pinched nerves and promotes an anti-inflammatory effect to restore flexibility to stiff and painful joints. When used on sports related injuries, such as when muscles, tendons or ligaments are damaged, it is thought that the solution speeds recovery through circulation by getting circulation to the damaged area quickly and preventing inflammation from building up to thereby assist athletes in recovering quickly. By reducing inflammation, the solution may restore flexibility to tight muscles or arthritic joints.

The unique combination of camphor and/or eucalyptus oil to the solution prevents the arnica montana and rosemary oil form separating quickly before application onto a person's skin. Furthermore, the presence of the emu oil in this solution assists penetration of the solution into the person's skin, thereby providing fast reduction of inflammation in the treated area.

The combination of the emu oil and rosemary oil and other ingredients in the solution ensures rapid penetration through the skin and assist the arnica and the other active ingredients in providing a therapeutic effect, as outlined above.

In other embodiments, the solution may be applied to the skin in a tincture and the composition may be applied as a cream, gel, ointment, milk or lotion.

It would be appreciated by a person skilled in the art that numerous variations and/or modifications may be made to the present invention as shown in the specific embodiments without departing from the spirit or scope of the invention as broadly described. The present embodiments are therefore, to be considered in all respects to be illustrative and not restrictive.

What is claimed is:

1. A therapeutic composition comprising:

arnica in the range of about 3% to about 8% by weight;

rosemary oil in the range of about 3% to about 15% by weight;

emu oil in the range of about 3% to about 8% by weight;

eucalyptus oil in the range of about 3% to about 8% by weight;

camphor in the range of about 2.6% to about 3.4% by weight; and ethanol in the range of about 72% to about 80% by weight.

2. A therapeutic composition comprising:

arnica in the range of about 3% to about 35% by weight;

rosemary oil in the range of about 3% to about 35% by weight;

emu oil in the range of about 0.5% to about 37% by weight;

eucalyptus oil in the range of about 0.4% to about 35% by weight;

camphor in the range of about 2.6% to about 35% by weight; and ethanol in the range of about 3% to about 85% by weight.

* * * * *